(12) United States Patent
Allen et al.

(10) Patent No.: US 8,951,599 B2
(45) Date of Patent: Feb. 10, 2015

(54) WOUND DRESSING

(71) Applicant: International Business Machines Corporation, Armonk, NY (US)

(72) Inventors: Robert D. Allen, San Jose, CA (US); Christopher E. Bannister, Raleigh, NC (US); Jere J. Brophy, Loveland, OH (US); Richard A. DiPietro, Campbell, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 13/677,573

(22) Filed: Nov. 15, 2012

(65) Prior Publication Data
US 2014/0113061 A1    Apr. 24, 2014

Related U.S. Application Data

(63) Continuation of application No. 13/655,090, filed on Oct. 18, 2012.

(51) Int. Cl.
| | |
|---|---|
| C08F 12/00 | (2006.01) |
| B05D 3/02 | (2006.01) |
| A61F 13/00 | (2006.01) |
| A61L 31/04 | (2006.01) |
| A61L 15/22 | (2006.01) |

(52) U.S. Cl.
CPC ............. *A61L 31/04* (2013.01); *A61L 15/225* (2013.01)
USPC ............. 427/2.31; 602/48; 602/43; 424/443; 424/447; 526/243

(58) Field of Classification Search
USPC .......................................................... 602/48
See application file for complete search history.

(56) References Cited

U.S. PATENT DOCUMENTS

| | | | | |
|---|---|---|---|---|
| 3,709,221 | A * | 1/1973 | Riely | 602/43 |
| 4,203,435 | A | 5/1980 | Krull et al. | |
| 4,860,737 | A | 8/1989 | Lang et al. | |
| 4,977,892 | A | 12/1990 | Ewall | |
| 5,382,639 | A * | 1/1995 | Moore et al. | 526/243 |
| 5,613,942 | A | 3/1997 | Lucast et al. | |
| 5,632,731 | A | 5/1997 | Patel | |
| 5,985,395 | A | 11/1999 | Comstock et al. | |
| 6,500,539 | B1 | 12/2002 | Chen et al. | |
| 6,818,253 | B2 * | 11/2004 | Kimbrell | 427/393.4 |
| 7,137,968 | B1 | 11/2006 | Burrell et al. | |
| 7,468,470 | B2 | 12/2008 | Bracht | |
| 7,678,537 | B2 * | 3/2010 | Allen et al. | 430/327 |
| 2002/0048679 | A1 * | 4/2002 | Lohmer et al. | 428/447 |

FOREIGN PATENT DOCUMENTS

| | | |
|---|---|---|
| CA | 2284096 A1 | 2/1998 |
| JP | 2011255215 A | 12/2011 |

* cited by examiner

*Primary Examiner* — Cachet Sellman
(74) *Attorney, Agent, or Firm* — Cantor Colburn LLP

(57) ABSTRACT

A wound dressing and a method of making the wound dressing is described herein. The wound dressing is formed of an absorbent substrate formed of one or more layers and a low-adherence layer disposed on the substrate. The low-adherence layer can be disposed within at least a portion of the substrate. The low-adherence layer is formed of a mixture of at least one highly fluorinated polymer and at least one acidic polymer. The at least one highly fluorinated polymer has a fluorine content greater than the fluorine content of the at least one acidic polymer.

29 Claims, 1 Drawing Sheet

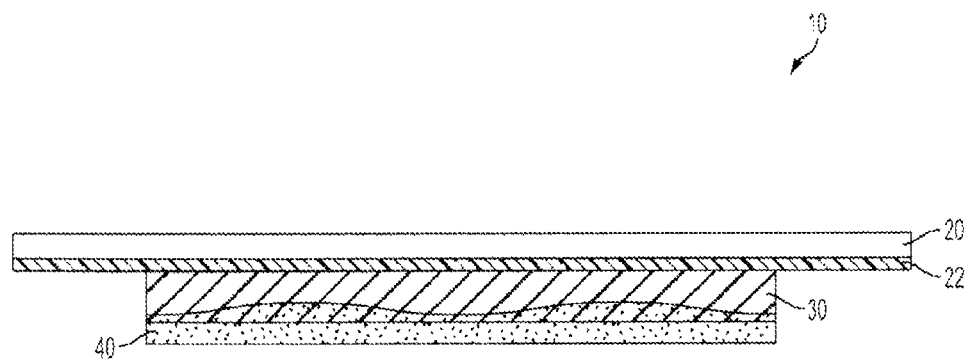

WOUND DRESSING

CROSS-REFERENCE TO RELATED APPLICATIONS

This application is a continuation of U.S. Non-Provisional application Ser. No. 13/655,090, entitled "NOVEL WOUND DRESSING", filed Oct. 18, 2012, which is incorporated herein by reference in its entirety.

TECHNICAL FIELD

The present invention relates generally to wound dressings. More specifically, the present invention relates to a multi-layer wound dressing employing a polymeric layer which does not stick to the wound and a wound pad comprising an absorbent and/or wicking material.

BACKGROUND

Modern bandages or wound dressings commonly are combinations of materials incorporating a suitable adhesive for the surrounding skin with a wound pad of absorbent material. The properties of the absorbent material vary with respect to the type of injury. Conventional wound dressings readily absorb fluids and can become saturated with exudate seeping from an open wound, necessitating frequent bandage or dressing changes. Frequent changes can cause wound irritation and discomfort to the patient. Thus, it is important for the wound pad to have minimal adherence to the healing wound.

Proteinaceous exudation from many types of skin lesions is normal during the healing process. Wounds which produce exudate include Stage II and Stage III ulcers, second and third degree burns, skin grafts and donor sites, deep derm abrasions, and lacerations. It is known that proteinaceous exudate acts as an adhesive or glue upon drying to adhere the dressing to the wound. In addition, there is a secondary mechanism of adherence in which new tissue grows into the structure of the wound dressing.

Generally, adherence of the proteinaceous exudate to the dressing is a function of the surface polarity of the material of the wound dressing in direct contact with the wound. Materials having a highly hydroxyl-rich surface, such as cotton gauze, adhere strongly while materials having substantially non-polar surfaces, such as nylon and silicones, do not. However, non-polar materials are less absorbent and trap exudates at the wound surface to retard the healing process.

Thus, there remains a need for a wound dressing which has the capability of absorbing proteinaceous exudate as it appears at the surface of an open wound and yet avoid adherence of the wound dressing to the wound. Accordingly, it is to solving this and other needs that the present invention is directed.

SUMMARY

The present invention is directed to a wound dressing which does not adhere to a wound surface or which has improved non-adhesion characteristics relative to the wound dressings known to the art. In accordance with the present invention, the wound dressing comprises an absorbent substrate and a low-adherence layer disposed on the substrate. In another aspect, the low-adherence layer is disposed within at least a portion of the substrate. The low-adherence layer comprises a mixture of at least one highly fluorinated polymer and at least one acidic polymer. Also, the at least one highly fluorinated polymer has a fluorine content greater than the fluorine content of the at least one acidic polymer. For example, the at least one highly fluorinated polymer can contain more than about 25 percent by weight fluorine. Also, the at least one highly fluorinated polymer can comprise a perfluoroisopropyl alcohol moiety.

The at least one highly fluorinated polymer has the structure of Structure I:

  (I)

wherein each monomer $A_1$ through $A_N$ is a monomer having a structure independently selected from Structures II, III, or IV, N is the average number of monomer units of the at least one highly fluorinated polymer, and Structures II, III, and IV, respectively, have the following structures:

  (II)

  (III)

  (IV)

wherein each $Z_1$, $Z_2$, $Z_3$, $R_1$, $R_2$, and $R_3$ are as defined below. In one aspect, $R_1$ is a perfluoroisopropyl alcohol moiety.

The at least one acidic polymer has the structure of Structure V:

  (V);

wherein each monomer $B_1$ through $B_M$ is a monomer having a structure independently selected from Structures VI, VII, or VIII, M is the average number of monomer units of the at least one acidic polymer, and Structures VI, VII, and VIII, respectively, have the following structures:

  (VI)

  (VII)

  (VIII)

wherein each $Z_4$, $Z_5$, $Z_6$, $R_4$, $R_5$, and $R_6$ are as defined below.

In another aspect, the low-adherence layer comprises a mixture of at least one class A polymer and at least one class B polymer. The at least one class A polymer has a fluorine content greater than the fluorine content of the at least one class B polymer. In addition, the at least one class A polymer has the structure of Structure IX and the at least one class B polymer has the structure of Structure X as follows:

(IX)
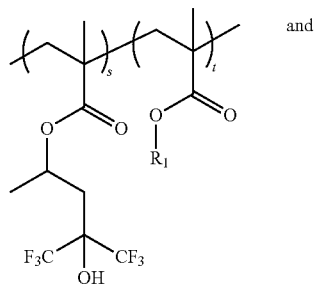
and
(X)
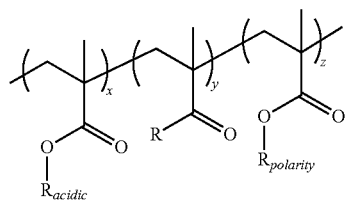
wherein R, $R_f$, $R_{acidic}$, and $R_{polarity}$ are as defined below. Example moieties for R include, but are not limited to:
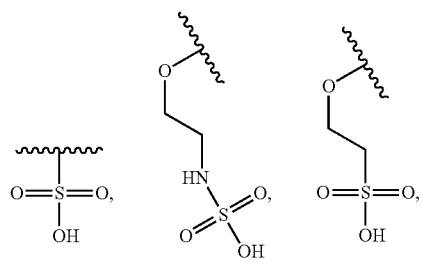
Examples of the $R_f$ moieties include, but are not limited to: —H, —CH$_3$,
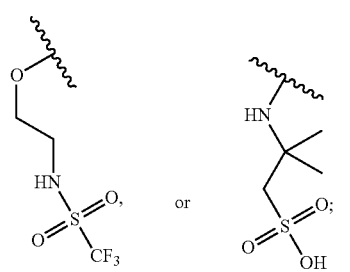
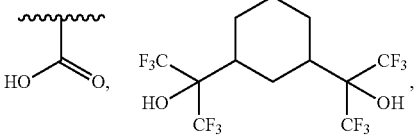
-continued
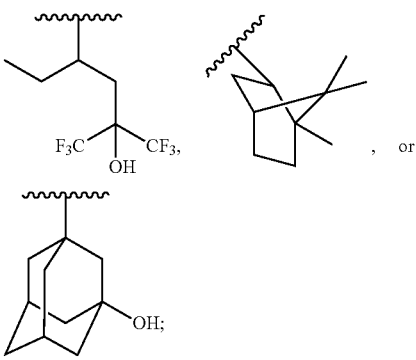
Examples of the $R_{acidic}$ moieties include, but are not limited to:
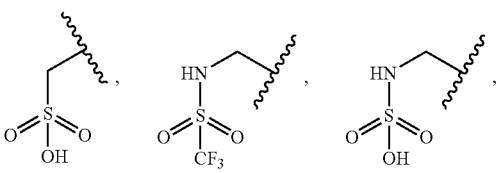
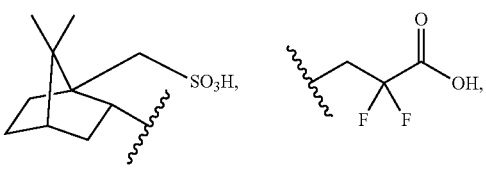
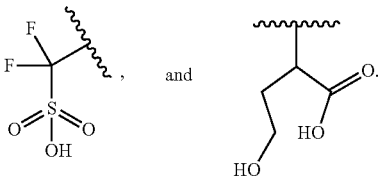
Examples of the $R_{polarity}$ moieties include, but are not limited to:
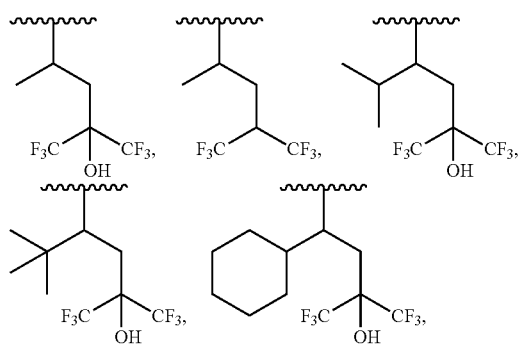
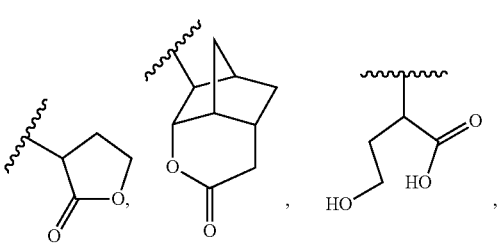

-continued

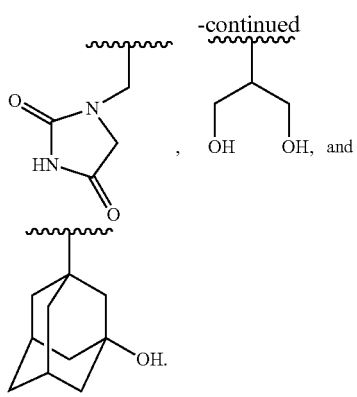

, OH OH, and

The substrate can be a woven fabric, a nonwoven fabric, a foam, or respective layers thereof in any combination. In another aspect, the substrate is a gauze, a net, a mesh, a fleece, a foam, or respective layers thereof in any combination. Yet, in another aspect, the substrate is formed of cotton, a cellulose derived polymer, a polyolefin, a polyester, a polyamide, a polyester, a polyurethane, a polybutadiene, an elastomer of polybutadiene or polyurethane, a polyacrylamide, a polyacrylonitrile, an acrylic, an acrylate, Karaya gum, a polysaccharide, or any combination thereof. Still, in another aspect, the substrate is a woven or nonwoven fabric comprising fibers formed of cellulose acetate, a polyester, nylon, rayon, a rayon/polyester blend, a polyester/cotton blend, cotton, or any combination thereof. Yet still, in another aspect, the substrate comprises a gauze formed of cotton, cellulose acetate, or a combination thereof.

Also disclosed herein is a method of making a wound dressing. The method comprises applying the low-adherence layer to an absorbent substrate to form a porous, absorbent wound dressing. In one aspect, the low-adherence layer penetrates and is disposed within at least a portion of the substrate.

It is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the present invention. It is important, therefore, that the claims be regarded as including such equivalent constructions insofar as they do not depart from the spirit and scope of the present invention.

Other advantages and capabilities of the invention will become apparent from the following description taken in conjunction with the accompanying drawings showing the embodiments and aspects of the present invention.

BRIEF DESCRIPTION OF THE SEVERAL VIEWS OF THE DRAWINGS

The disclosure below makes reference to the annexed drawing wherein:

FIG. 1 is cross-sectional view of a wound dressing made in accordance with the present invention.

DETAILED DESCRIPTION

The term "anti-biologic" as used herein includes any substance which has an effect on a biological organism. In particular, an anti-biologic substance includes, but is not limited to, bactericides, antibiotics, fungicides, herbicides, antimicrobials, and similar substances which effect biological organisms, both animal and plant.

The term "dressing" as used herein includes any material applied to protect, cushion, cover, and generally guard a wound from either further injury or from any desirable contacts. The material can be in any form such as a pad, gauze, cloth, sheet, or similar form as might be used in the medical arts. The dressing can be used by itself or in conjunction with a medicinal or other substance applied thereto or contained therein, and can comprise one or more layers.

The terms "non-stick," "no-stick," "anti-adherent," "non-adherent," "anti-adhesion," variations thereof, and similar terms, can be used interchangeably to signify a dressing which either does not stick or adhere to a wound or which exhibits a reduced tendency to stick or adhere to a wound relative to other dressings.

As described herein, the present invention provides a wound dressing comprising a wound facing low-adherence layer, at least one absorbent layer, and, optionally, an outer layer. The low-adherence layer, described in detail below, comprises a porous, conformable film disposed on and penetrating at least a portion of the absorbent layer. The absorbent layer comprises a conformable hydrophilic woven fabric, a hydrophilic nonwoven fabric, hydrophilic foam, or any combination thereof. The outer layer, when present, comprises a conformable film that permits moisture vapor transmission, a conformable elastically extensible net, or a conformable backing material, such as a film or a woven fabric known in the art for such purpose. In addition the outer layer can have an adhesive layer on one surface thereof to engage the skin of a patient. In one aspect, the outer layer can be used to regulate moisture loss from the wound area under the dressing and also to act as a barrier to bacteria to delay or prevent bacteria on the outside surface of the dressing penetrating to the wound area. In another aspect, the outer layer comprises a conformable microporous film. Although not required, the component layers of the wound dressing can have a porosity such that moisture contained in the exudate can pass through the dressing at a desired rate and be evaporated therefrom, thereby extending the useful life of the dressing.

Typically, the adhesive layer comprises a pressure-sensitive adhesive material disposed on the outer layer on the surface thereof facing the absorbent layer. The adhesive can be disposed on the outer layer in one or more positions to removably affix the wound dressing to the patient. In this aspect, the wound dressing is an "island dressing," wherein the absorbent layer is substantially centrally disposed with respect to an adhesive layer of greater dimensions so that free adhesive surface surrounds the periphery of the absorbent layer for securing the dressing to the skin. It is desirable for the adhesive material to comprise a composition that adheres to the healthy skin of the patient, but tends not to adhere to the open wound itself. For example, by fixing a self-adhering adhesive at the periphery or on two edges of the wound dressing, typically on the outer layer when present, an immediate and final placing over the wound is achieved so that slipping is prevented.

In another aspect, the wound dressing comprises the wound facing low-adherence layer, the at least one absorbent layer, a topically effective anti-biologic disposed in the at least one absorbent layer, the optional outer layer, and, optionally, the adhesive layer described immediately above. Although not required, the layers of the wound dressing can be attached in a contiguous and co-extensive manner in the form of a laminate.

As indicated above, the low-adherence layer is to be positioned directly on the wound area of the patient. Since the low-adherence layer is anti-adherent to proteinaceous exudate, skin maceration is minimized. The exudate passes through the porous low-adherence layer to be absorbed by the at least one absorbent layer. In another aspect, the at least one absorbent layer can permit transpiration of water vapor from the exudate to the atmosphere without the low-adherence layer subsequently adhering to the wound. Further, the low-adherence layer can have a substantially smooth surface, which provides a wound dressing that is less irritating to the skin than some commercially available gauze. By structuring of the surface of the low-adherence layer contacting the wound, an additional reduction in adherence to the skin and wound can be achieved with the absorbability of the at least one absorbent layer remaining substantially unchanged. Additionally, air channels formed by the structuring further the healing process.

The wound dressing of this invention can be in any convenient form of shape or size. In one aspect, the wound dressing is a pad of rectangular shape. In another aspect, the wound dressing is a pad of circular shape. Yet, in another aspect, the wound dressing is a pad of oval shape. Still, in another aspect, the wound dressing is a pad of square shape. In addition, the wound dressing can be an elongate strip which can be used as a bandage or can be used to prepare smaller dressings.

In another aspect, the wound dressing can be in the form of a laminate. For example, individual layers of the wound dressing can be formed into a laminate by bonding the layers together in one or more laminating processes, with the exception of the low-adherence layer. To recall, the low-adherence layer is disposed on and penetrates at least a portion of the at least one absorbent layer and thus, is already bonded to the at least one absorbent layer. Suitable bonding methods include heat sealing or adhesive bonding. Typically, a bonding layer comprising an adhesive is disposed between the respective layers of the absorbent layer and the outer layer. Such bonding layer is discontinuous. Discontinuous adhesive bonding of the layers permits moisture vapor transmission and allows the passage of proteinaceous exudate from the wound to the at least one absorbent layer. Adhesive bonding compositions which can be employed to form a laminated wound dressing include, but are not limited to, acrylate ester copolymers and polyvinyl ethyl ethers. Any adhesive suitable for use in medical applications can be employed to form the laminate.

In one aspect, the laminate can be formed by heat sealing. The outer layer and the at least one absorbent layer, to include multiple layers of absorbent materials, can be heat sealed to one another by heat and pressure in a conventional manner in one or more laminating processes by respective bonding layers. For example, the outer layer can be contacted with the at least one absorbent layer, either with or without the presence of the low-adherence layer, through the respective nips of laminating roller sets under low pressure and at a temperature sufficient to permit the adhesive of the bonding layer to bond the layers of the at least one absorbent layer and the outside layer, when present, together. Multiple laminating roller sets can be employed, if desired.

In another aspect, the laminate can be formed by ultrasonic welding. A polymeric material which is amenable to ultrasonic welding, i.e., a material will melt on the application of localized heat generated by ultrasonic acoustic vibrations and then fuse the layers together on cooling, can be employed as the bonding layer.

It is desirable for the wound dressing to be sterile. For example, the sterile wound dressing can be packaged in bacteria impervious pouches. Such packages can be prepared under aseptic conditions or alternatively sterilized after packing by a conventional procedure including, but not limited to, heat sterilization, for example by steam, ethylene oxide sterilization, or gamma irradiation. To assist in maintaining the sterilization of the wound dressing, the low-adherence layer can be covered with a release paper.

It is not required for the wound dressing to have an adhesive layer to affix the dressing to the skin of the patient. The wound dressing can be removably attached to the patient with an adhesive tape, a gauze wrap, a wrap made of an expandable material, e.g. an "ace bandage," and the like.

The Absorbent Layer

The absorbent layer can comprise one or more layers of absorbent and/or wicking materials capable of being employed in wound dressings to receive proteinaceous exudate from a wound. In one aspect, the absorbent layer is a flexible high-lofted, non-toxic fabric which has sufficient structural integrity to withstand normal handling, processing, and use. In another aspect, the absorbent layer is formed of a perforated material which allows exudate to penetrate or diffuse therein. The perforated material can comprise a woven or non-woven fabric such as cotton, gauze, a polymeric net or mesh such as polyethylene, nylon, polypropylene, or polyester, an elastomer such as polyurethane or polybutadiene elastomers, or a foam such as open cell polyurethane foam.

For example, the absorbent layer can comprise a woven or nonwoven fabric formed of non-toxic fibers. In another aspect, the non-toxic fibers have a highly hydroxyl-rich surface. Fibers which can be employed to form the absorbent layer include, but are not limited to, cotton, nylon, rayon, polyester, and polyester cellulose fibers. Should the absorbent layer include a layer of a nonwoven fabric, such nonwoven can be a spun-bonded or spun-laced construction. Further, wet-laid and air-laid non-woven fabrics can be employed. Although not required, fabric forming a layer of the absorbent layer can have numerous fibers protruding from its surfaces. Such protruding fibers are beneficial for bonding of either the low-adherence layer and/or the adhesive layer to the fabric to facilitate a secure mechanical bond therebetween. In one aspect, a pad formed of cotton gauze comprises the absorbent layer. In another aspect, the absorbent layer comprises a spun-bonded polyester staple fiber fabric. Still, in another aspect, the absorbent layer comprises a woven or a nonwoven fabric formed of cellulose acetate. Further, any layer forming the absorbent layer can comprise a fabric formed of any combination of fibers suitable for use in medical dressings. Such fibers include, but are not limited to, cellulose acetate, polyester, polyolefin, polyamide, cotton, and blends thereof. In another aspect, the fibers forming the absorbent layer include, but are not limited to, rayon, rayon/polyester, polyester/cotton blends, cotton, cellulosic materials, etc.

Moreover, the absorbent layer can comprise a hydrophilic material capable of retaining its integrity even after absorbing 2 to 20 times its weight of exudate. Such hydrophilic materials include, but are not limited to, sodium carboxymethylcellulose, various polyacrylamide, polyacrylonitrile and acrylic acid polymers, Karaya gum, and polysaccharides. Acrylics and acrylates, which are unsubstituted or variously substituted, can be employed in the absorbent layer.

In addition, the absorbent layer can comprise a fleece material. Fleece material typically contains fibers of polypropylene, polyesters, polyethylene, polyamides, and any combination thereof.

As indicated above, the absorbent layer can comprise a hydrophilic polymer foam. Such foam layer absorbs wound exudate rapidly and enhances the low adherency properties of the low-adherence layer. For example, rapid absorption of exudate substantially avoids undesirable pooling of exudate between the low-adherence layer and the wound. The ability of open cell hydrophilic polymer foam layers to absorb and retain fluids depends to some extent on the size of the foam cells, the porosity of the foam and the thickness of the foam layer. Apt sizes of the foam cells, cell membrane opening areas and thicknesses of the foam are known in the medical arts. The use of hydrophilic polymer foams in the absorbent layer can allow the wound to be maintained in a moist condition even when exudate is absorbed and removed from the wound surface.

The Adhesive Layer

The adhesive layer can be formed of any sterial, pressure-sensitive, not-toxic, adhesive suitable for adhesion to healthy normal human skin employed in wound dressing applications. While the adhesive layer adheres to normal healthy skin, the adhesive should have substantially little or no tendency to adhere to the open wound. Accordingly, potential interference with normal healing and trauma to the neoepithelium on removal of the dressing is minimized. Adhesive sterilization can be conducted by any conventional means, such as radiation, e.g., gamma ray or electron beam irradiation, thermal or steam processes. Examples of suitable pressure-sensitive adhesives include, but are not limited to, polyacrylic skin adhesives, polyvinyl ether adhesives, and polyurethane adhesives.

The Anti-Biologic

As indicated above, the wound dressing can contain a topically effective anti-biologic disposed in the at least one absorbent layer in a therapeutically effective amount. In one aspect, the anti-biologic is a bactericide. For example, the bactericide is a broad spectrum antibacterial agent such as a silver salt for example silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as benzalkonium chloride or the like.

The process used to incorporate anti-biologics into a fiber is well known in the art. See, for example, U.S. Pat. Nos. 3,959,556 and 4,343,853 to Morrison. These references describe the incorporation of an antimicrobial agent into a thermoplastic resin to produce a fiber having the antimicrobial intimately mixed with the resin.

The Low-Adherence Layer

As discussed above, the present invention employs a non-homogenous low-adherence (LA) layer comprising a mixture of at least one highly fluorinated polymer (class A polymer) and at least one acidic polymer (class B polymer). In accordance with the present invention, the fluorine content of the class A polymer is greater than the fluorine content of the class B polymer. Class A polymers, class B polymers, and mixtures thereof employed in the present invention, and methods of making such polymers and mixtures are described in U.S. Pat. No. 7,678,537 to Allen et al., which is incorporated herein by reference in its entirety. Class A and B polymers are miscible with one other and can be disposed on the absorbent layer. Each polymer of the mixture segregates to the interface for which it was designed. The lower surface energy, more highly fluorinated class A polymer is at its maximum molar concentration in the LA layer at the air/LA layer interface and at its minimum molar concentration in the LA layer at the LA layer/absorbent layer interface. The acidic class B polymer is at its minimum molar concentration in the LA layer at the air/LA layer interface and at its maximum molar concentration in the LA layer/absorbent layer interface. For example, the weight percentage of type A polymer can be greater than the weight percentage of type B polymer at the LA layer to air interface. In another aspect, the weight percentage of type B polymer can be greater than the weight percentage of type A polymer at the LA layer to absorbent layer interface.

The class A polymer has a high fluorine content for surface energy control and high water contact angles and includes an acidic pendent group(s). The class B polymer has a highly acidic pendent group(s), e.g. sulfonic acid, and one or more acidic pendent group(s) different from the highly acidic pendent group(s). Typically, the class A and B polymers are soluble in the same solvent(s).

An acidic group is defined as a group having a p$K_a$ less than that of water. The p$K_a$ of water is slightly greater than 15 (as measured in water) or 31 (as measured in dimethylsulfoxide). In one aspect, acidic groups have a p$K_a$ (negative log of the acid dissociation constant) less than about 13 (as measured in water) or 24 (as measured in dimethylsulfoxide). A strongly acidic group is defined as a group having a p$K_a$ of less than about 3 (as measured in water) or 8 (as measured in dimethylsulfoxide). A highly fluorinated polymer is defined as a polymer containing more than about 25 percent by weight fluorine. A polymer with low fluorine content is defined as a polymer containing less than about 15 percent by weight fluorine. A polymer with moderate fluorine content is defined as a polymer containing between than about 15 percent by weight fluorine and about 25 percent by weight fluorine. A fluoroalcohol is defined as an organic compound bearing a hydroxyl group wherein one or more non-hydroxyl group hydrogen atoms are replaced with fluorine atoms. The fluoroalcohol may be comprised of a linear, branched, cyclic, polycyclic, or aromatic structure. Many non-limiting examples of such fluoroalcohols may be found in H. Ito, "Chemical Amplification Resists for Microlithography," *Adv. Polym. Sci.* 2005, 172, 37-245.

Class A polymers employed in the LA layer have the structure:

(I)

wherein each monomer $A_1$ through $A_N$ is a monomer independently having a structure of Structures II, III, or IV described below. Structure I should not be interpreted as meaning all polymers in a given sample of a class A polymer have the same number of monomer units, but rather N can vary between individual polymers. N could also be thought of as being the average number of monomer units in a given sample of class A polymers.

Class A polymers comprise one or more different monomers having the following structures:

(II)

(III)

(IV)

wherein each $Z_1$, $Z_2$, and $Z_3$ is independently a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, a carbonate group, an acetal group, a ketal group, a siloxyl group, a carboxylic acid group, a carboxylic acid anhydride group, a carboxylic acid anhydride half-ester group, an ether group, an amide group, a carbamate group, a thioether group, a fluorinated linear alkylene, a fluorinated branched alkylene, a fluorinated cyclic alkylene, a polycyclic alkylene, a fluorinated linear heteroalkylene, a fluorinated branched heteroalkylene, a fluorinated cyclic heteroalkylene, a fluorinated polycyclic heteroalkylene, a fluorinated ester group, a fluorinated carbonyl group, a fluorinated carbonate group, a fluorinated acetal group, a fluorinated ketal group, a fluorinated siloxyl group, a fluorinated carboxylic acid group, a fluorinated carboxylic acid anhydride group, a fluorinated carboxylic acid anhydride half-ester group, a fluorinated ether group, a fluorinated amide group, a fluorinated carbamate group, or a fluorinated thioether group;

wherein $R_1$ is a fluoroalcohol group, a fluoroalcohol group protected with an acid-labile group, a fluoroalcohol group protected with a base-labile group, a fluoroalcohol group protected with an acid-labile fluorinated group, a fluoroalcohol group protected with a base-labile fluorinated group, a lactone group, a $C_5$ to $C_{10}$ aromatic or heteroaromatic group, or an —$X_1$—$Y_1$ group, wherein $X_1$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, an amide group, an ether group, a thioether group, a carbonate group, a carbamate group, an acetal group, or a ketal group and $Y_1$ is a fluoroalcohol group, a fluoroalcohol group protected with an acid-labile group a fluoroalcohol group protected with a base-labile group, a fluoroalcohol group protected with an acid-labile fluorinated group, or a fluoroalcohol group protected with a base-labile fluorinated group;

wherein $R_2$ is hydrogen, fluorine, a fluoroalcohol group, a sulfonamide group, a phenolic group, a naphtholic group, a carboxylic acid group, a sulfonic acid group, a $C_5$ to $C_{10}$ aromatic or heteroaromatic group, or an —$X_2$—$Y_2$ group, wherein $X_2$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_2$ is a fluoroalcohol group, a sulfonamide group, a phenolic group, a naphtholic group, a carboxylic acid group, or a sulfonic acid group;

wherein $R_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycylic heteroalkane, a $C_5$ to $C_{10}$ aromatic or heteroaromatic group, or a —$X_3$—$Y_3$ group, wherein $X_3$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

In another aspect, $R_1$ is a perfluoroisopropyl alcohol moiety. While not wishing to be bound by theory, it is believed the perfluoroisopropyl alcohol moiety, when incorporated into the class A polymer structure, provides an ability to tailor the hydrophobic/hydrophilic nature of the resulting LA layer mixture.

Class B polymers may be described as having the structure:

wherein each monomer $B_1$ through $B_M$ is a monomer independently having a structure of VI, VII, or VIII described below. Structure V should not be interpreted as meaning all polymers in a given sample of a class B polymer have the same number of monomer units, but rather M can vary between individual polymers. M could also be thought of as being the average number of polymer units in a given sample of class B polymers.

Class B polymers comprise one or more different monomers having the following structures:

wherein each $Z_4$, $Z_5$, and $Z_6$ is independently a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, a carbonate group, an acetal group, a ketal group, a siloxyl group, a carboxylic acid group, a carboxylic acid anhydride group, a carboxylic acid anhydride half-ester group, an ether group, an amide group, a carbamate group, a thioether group, a fluorinated linear alkylene, a fluorinated branched alkylene, a fluorinated cyclic alkylene, a polycyclic alkylene, a fluorinated linear heteroalkylene, a fluorinated branched heteroalkylene, a fluorinated cyclic heteroalkylene, a fluorinated polycyclic heteroalkylene, a fluorinated ester group, a fluorinated carbonyl group, a fluorinated carbonate group, a fluorinated acetal group, a fluorinated ketal group, a fluorinated siloxyl group, a fluorinated carboxylic acid group, a fluorinated carboxylic acid anhydride group, a fluorinated carboxylic acid anhydride half-ester group, a fluorinated ether group, a fluorinated amide group, a fluorinated carbamate group, or a fluorinated thioether group;

wherein $R_4$ is a sulfonic acid group, a sulfinic acid group, a carboxylic acid group, a $C_5$ to $C_{10}$ aromatic or heteroaromatic group, or a —$X_4$—$Y_4$ group, wherein $X_4$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, an amide group, an ether group, a thioether group, a carbonate group, a carbamate group, an acetal group, or a ketal group and $Y_4$ is a sulfonic acid group, a sulfinic acid group, or a carboxylic acid group;

wherein $R_5$ is hydrogen, fluorine, a fluoroalcohol group, a sulfonamide group, a phenolic group, a naphtholic group, a carboxylic acid group, a sulfonic acid group, a lactone group, a $C_5$ to $C_{10}$ aromatic or heteroaromatic group, or a —$X_5$—$Y_5$ group, wherein $X_5$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, an amide group, an ether group, a thioether group, a carbonate group, a carbamate group, an acetal group, or a ketal group and $Y_5$ is a fluoroalcohol group, a sulfonamide group, a phenolic group, a naphtholic group, a carboxylic acid group, or a sulfonic acid group; and wherein $R_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycylic heteroalkane, a $C_5$ to $C_{10}$ aromatic or heteroaromatic group, or an —$X_6$—$Y_6$ group, wherein $X_6$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

In another aspect, the LA layer comprises a mixture of class A polymers and class B polymers of structures IX and X, respectively:

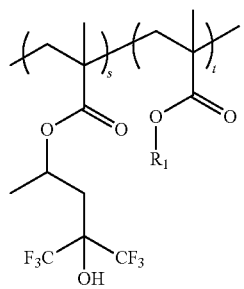

(IX) and

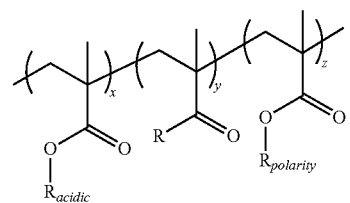

(X)

wherein $R_f$ is selected from $R_1$, $R_2$, or $R_3$ as defined above; $R_{acidic}$ is selected from $R_4$ or $R_5$ as defined above; $R_{polarity}$ is different from $R_{acidic}$ and selected from $R_5$ or $R_6$ as defined above; R is different from $R_{acidic}$ and $R_{polarity}$ and is selected from $R_5$; s is any number from 0 to 100 and t is any number from 0 to 100, such that s+t is greater than or equal to 50 and less than or equal to 100; and x is any number from 0 to 99.9, y is any number from 0.1 to 99.9, and z is any number from 0 to 99.9, such that x+y+z is greater than or equal to 50 and less than or equal to 100.

Examples of the R moiety include, but are not limited to:

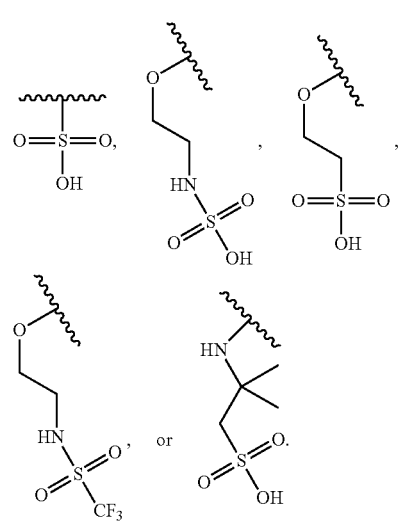

In another aspect, R is

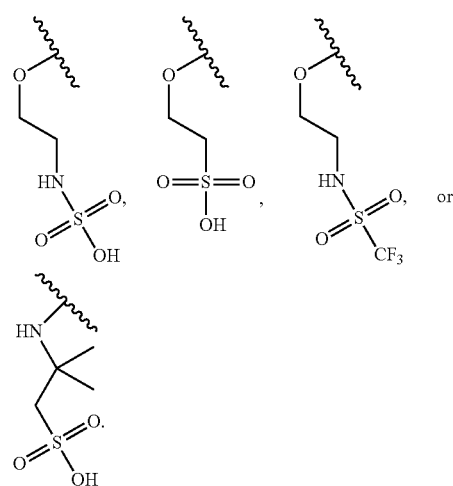

Still, in another aspect, R is

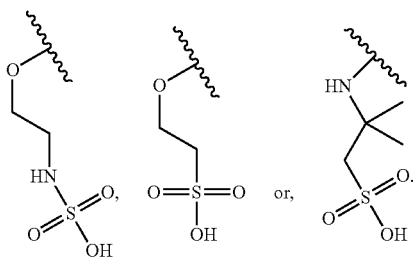

Yet, in another aspect, R is

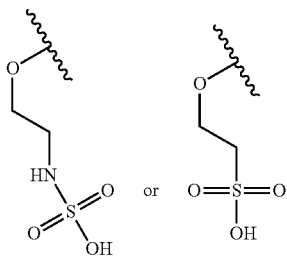 [SMILES: *OCCNS(=O)(=O)O ; *OCCS(=O)(=O)O]

Examples of the $R_f$ moiety include, but are not limited to: —H, —CH$_3$,

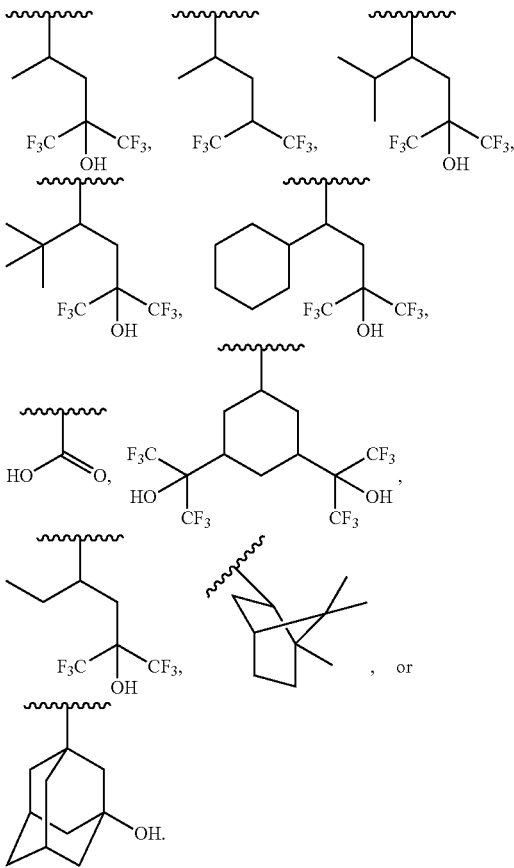

Examples of the $R_{acidic}$ moieties include, but are not limited to:

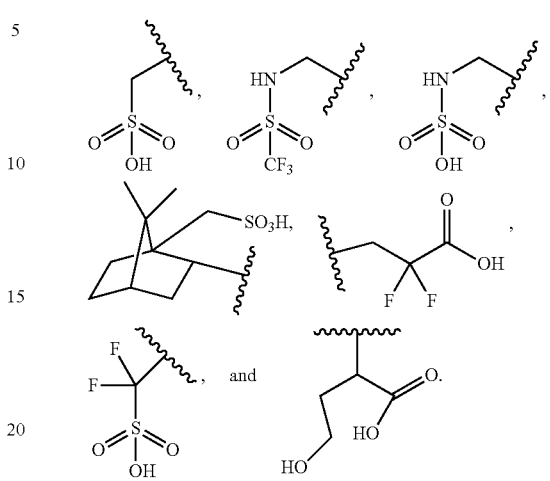

Examples of the $R_{polarity}$ moieties include, but are not limited to:

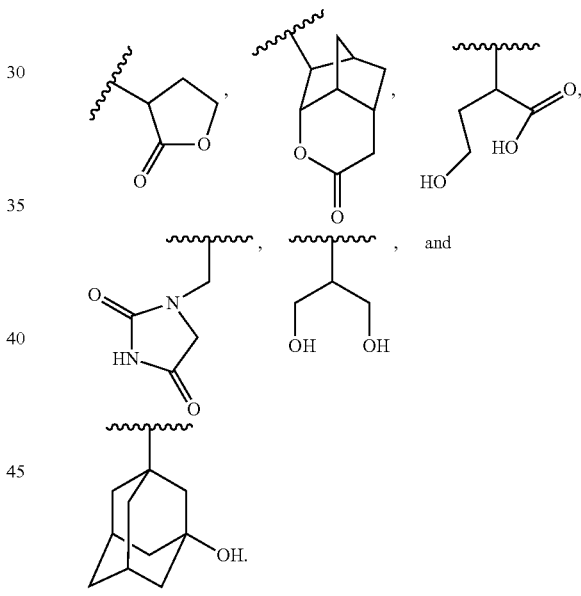

Class A polymers of the present invention can include any combination of s mer % of the perfluoroisopropyl alcohol moiety and t mer % of the ester moiety. Class B polymers of the present invention can include any combination of x mer % of the $R_{acidic}$ ester moiety, y mer % of the sulfonic acid moiety, and z mer % of the $R_{polarity}$ ester moiety. A mer is defined as a chemical repeat unit in the polymer. Mer fraction is defined as the number of mers of all repeat units in a polymer. Mer % is defined as the mer fraction and multiplied by 100. Accordingly, the total amount of all Mers is 100%. For example, in one aspect, s is 95 and t is 5. In another aspect, s is 80 and t is 20.

In one aspect, mixtures employed to form the LA layer in accordance with the present invention can be mixtures where the class A polymer is independently selected from homopolymers, copolymers, or terpolymers and the class B polymer is independently selected from single monomer polymers, copolymers, and terpolymers, as two or more of the properties imparted to the class A polymer by individual $R_1$, $R_2$, $R_3$ groups can be fulfilled by one or two R groups and two or more of the properties imparted to the class B polymer by individual $R_4$, $R_5$, $R_6$ groups may be fulfilled by one or two R groups. For example, the class A polymer can be a terpolymer where $R_1$ is selected to provide solubility in a desired solvent, $R_2$ is selected to tune the solubility in the selected solvent, and $R_3$ is selected to tune the surface energy and the class B polymer is a terpolymer where $R_4$ is a strongly acidic group, $R_5$ is a weak acidic group, and $R_6$ is selected to tune the polarity of the class B polymer.

Typically, although not required, the average molecular weight for class A and class B polymers is between about 500 and about 200,000, respectively. In another aspect, the average molecular weight for class A and class B polymers is between about 1000 and about 20,000, respectively.

Besides class A polymers and class B polymers, the LA layer mixtures can contain solvents, surfactants, stabilizers, other processing aides, and antimicrobials. The mixture of A and B class polymers are dissolved in a solvent to form a coating solution. The solvent can comprise one solvent or two or more different volatile solvents. Such solvents are not included in total solids calculations. Further, the stabilizers, surfactants and other additives (if any) can be added to the coating solution. In one example, surfactants comprise less than about 1 percent by weight of the totals solids content of the coating solution. In one example, stabilizers and other additives together comprise less than about 10 percent by weight of the total solids content of the coating solution. In one aspect, class A and class type B polymers together comprise between about 5 percent by weight to about 10 percent by weight of the coating solution. In another aspect, class A and class B polymers together comprise between about 2 percent by weight to about 15 percent by weight of the coating solution. Yet, in another aspect, class A and class B polymers together comprise up to about 30 percent by weight of the coating solution. Coating solutions can be made by adding dry (e.g., in powder form) class A and class B polymers to the solvent. Solvent extraction can be used to purify class A and class B polymers and then the solutions with the polymer (with or without a concentration procedure) mixed together to form a simple coating solution. Surfactants, stabilizers, and other additives can be added to the simple coating solution as solids or as solutions of dissolved solids to form a more complex coating solution. Additives and impurities which can stop formation of a vertically graded non-homogenous layer of class A and B polymers are excluded from being included or added to the coating solution.

For a fuller understanding of this disclosure and the invention described therein, reference should be made to the above and following detailed description taken in connection with the accompanying FIGURE. As illustrated in FIG. 1, the wound dressing 10 has an outer layer 20 (which is optional) disposed on one side of at least one absorbent layer 30, and a low-adherence layer 40 disposed on the other side of the absorbent layer 30. The outer layer 20 can have an adhesive layer 22 comprising a conventional adhesive known in the art to adhere the outer layer 20 to the absorbent layer 30. The adhesive forming the adhesive layer 22 can be a conventional pressure sensitive adhesive. As illustrated, the outer layer 20 and adhesive layer 22 extend beyond the absorbent layer 30 such that the adhesive layer 22 can engage the skin of a patient. A release layer (not shown) can be disposed over and releasably secured to the exposed surface of adhesive layer 22 to protect adhesive layer 22 during storage of dressing 10. The release layer is removed just prior to the application of dressing 10 over the wound.

The wound dressing 10 is manufactured by applying the polymer mixture of the low-adherence layer 40 described above which is in a flowable or sprayable form to a surface of the absorbent layer 30. The polymer mixture may be applied onto all or a portion of a surface of the low-adherence layer 40 using conventional techniques, such as printing, dipping, spraying, melt extruding, coating (e.g., solvent coating, powder coating, brush coating, etc.), and so forth. The polymer mixture penetrates at least a portion of the absorbent layer 30 and encapsulated fibers positioned at and immediately below the surface receiving the low-adherence layer 40. In one aspect, the polymer mixture penetrates the absorbent layer to a depth of about 1-2 millimeters. After curing, i.e. allowing the polymer mixture to form into a non-flowable state, e.g., solvent removal from the polymer mixture, by drying or evaporation, cooling from a flowable state to a non-flowable state, etc., the polymer mixture forms into the low-adherence layer 40 described above to produce the wound dressing 10. Since the polymer mixture coats the fibers of the porous absorbent layer surface, the low-adherence layer 40 is likewise porous, thereby allowing bodily fluids to pass through the low-adherence layer, which has a hydrophobic surface, and to be absorbed by the hydrophilic absorbent layer.

The foregoing is considered as illustrative only of the principles of the invention. Various modifications may be made of the invention without departing from the scope thereof and it is desired, therefore, that only such limitations shall be placed thereon as are imposed by the prior art and which are set forth in the appended claims.

The invention claimed is:

1. A method of making a wound dressing comprising:
applying a mixture of at least one highly fluorinated polymer and at least one acidic polymer onto a surface of an absorbent substrate, the at least one highly fluorinated polymer having a fluorine content greater than the fluorine content of the at least one acidic polymer and the at least one highly fluorinated polymer comprising a perfluoroisopropyl alcohol moiety; and
curing the polymer mixture disposed on the absorbent substrate to form a low-adherence layer.

2. The method of claim 1, wherein the low-adherence layer is disposed within at least a portion of the substrate.

3. The method of claim 1, wherein the at least one highly fluorinated polymer contains more than about 25 percent by weight fluorine.

4. The method of claim 1, wherein the at least one highly fluorinated polymer has the structure of Structure I:

wherein each monomer $A_1$ through $A_N$ is a monomer having a structure independently selected from Structures II, III, or IV, N is the average number of monomer units of the at least one highly fluorinated polymer, Structures II, III, and IV, respectively, have the following structures:

-continued

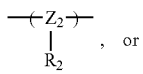 , or (III)

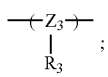 ; (IV)

wherein each $Z_1$, $Z_2$, and $Z_3$ is independently a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, a carbonate group, an acetal group, a ketal group, a siloxyl group, a carboxylic acid group, a carboxylic acid anhydride group, a carboxylic acid anhydride half-ester group, an ether group, an amide group, a carbamate group, a thioether group, a fluorinated linear alkylene, a fluorinated branched alkylene, a fluorinated cyclic alkylene, a polycyclic alkylene, a fluorinated linear heteroalkylene, a fluorinated branched heteroalkylene, a fluorinated cyclic heteroalkylene, a fluorinated polycyclic heteroalkylene, a fluorinated ester group, a fluorinated carbonyl group, a fluorinated carbonate group, a fluorinated acetal group, a fluorinated ketal group, a fluorinated siloxyl group, a fluorinated carboxylic acid group, a fluorinated carboxylic acid anhydride group, a fluorinated carboxylic acid anhydride half-ester group, a fluorinated ether group, a fluorinated amide group, a fluorinated carbamate group, or a fluorinated thioether group;

wherein $R_1$ is a fluoroalcohol group, a fluoro alcohol group protected with an acid-labile group, a fluoro alcohol group protected with a base-labile group, a fluoroalcohol group protected with an acid-labile fluorinated group, a fluoro alcohol group protected with a base-labile fluorinated group, a lactone group, a $C_5$ to $C_{10}$ aromatic or heteroaromatic group, or an —$X_1$—$Y_1$ group, wherein $X_1$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_1$ is a fluoroalcohol group, a fluoro alcohol group protected with an acid-labile group a fluoro alcohol group protected with a base-labile group, a fluoroalcohol group protected with an acid-labile fluorinated group, or a fluoroalcohol group protected with a base-labile fluorinated group;

wherein $R_2$ is hydrogen, fluorine, a fluoro alcohol group, a sulfonamide group, a phenolic group, a naphtholic group, a carboxylic acid group, a sulfonic acid group, a $C_5$ to $C_{10}$ aromatic or hetero aromatic group, or an —$X_2$—$Y_2$ group, wherein $X_2$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_2$ is a fluoroalcohol group, a sulfonamide group, a phenolic group, a naphtholic group, a carboxylic acid group, or a sulfonic acid group;

wherein $R_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycyclic heteroalkane, a $C_5$ to $C_{10}$ aromatic or heteroaromatic group, or a —$X_3$—$Y_3$ group, wherein $X_3$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

5. The method of claim 4, wherein $R_1$ is a perfluoroisopropyl alcohol moiety.

6. The method of claim 1, wherein the at least one acidic polymer has the structure of Structure V:

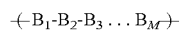 (V);

wherein each monomer $B_1$ through $B_M$ is a monomer having a structure independently selected from Structures VI, VII, or VIII, M is the average number of monomer units of the at least one acidic polymer, Structures VI, VII, and VIII, respectively, have the following structures:

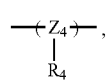 , (VI)

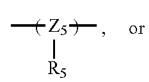 , or (VII)

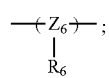 ; (VIII)

wherein each $Z_4$, $Z_5$, and $Z_6$ is independently a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, a carbonate group, an acetal group, a ketal group, a siloxyl group, a carboxylic acid group, a carboxylic acid anhydride group, a carboxylic acid anhydride half-ester group, an ether group, an amide group, a carbamate group, a thioether group, a fluorinated linear alkylene, a fluorinated branched alkylene, a fluorinated cyclic alkylene, a polycyclic alkylene, a fluorinated linear heteroalkylene, a fluorinated branched heteroalkylene, a fluorinated cyclic heteroalkylene, a fluorinated polycyclic heteroalkylene, a fluorinated ester group, a fluorinated carbonyl group, a fluorinated carbonate group, a fluorinated acetal group, a fluorinated ketal group, a fluorinated siloxyl group, a fluorinated carboxylic acid group, a fluorinated carboxylic acid anhydride group, a fluorinated carboxylic acid anhydride half-ester group, a fluorinated ether group, a fluorinated amide group, a fluorinated carbamate group, or a fluorinated thioether group;

wherein $R_4$ is a sulfonic acid group, a sulfinic acid group, a carboxylic acid group, a $C_5$ to $C_{10}$ aromatic or hetero aromatic group, or a $—X_4—Y_4$ group, wherein $X_4$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl groups, an amide group, an ether group, a thioether group, a carbonate group, a carbamate group, an acetal group, or a ketal group and $Y_4$ is a sulfonic acid group, a sulfinic acid group, or a carboxylic acid group;

wherein $R_5$ is hydrogen, fluorine, a fluoroalcohol group, a sulfonamide group, a phenolic group, a naphtholic group, a carboxylic acid group, a sulfonic acid group, a lactone group, a $C_5$ to $C_{10}$ aromatic or heteroaromatic group, or a $—X_5—Y_5$ group, wherein $X_5$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, an amide group, an ether group, a thioether group, a carbonate group, a carbamate group, an acetal group, or a ketal group and $Y_5$ is a fluoroalcohol group, a sulfonamide group, a phenolic group, a naphtholic group, a carboxylic acid group, or a sulfonic acid group; and wherein $R_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycyclic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycylic heteroalkane, a $C_5$ to $C_{10}$ aromatic or heteroaromatic group, or an $—X_6—Y_6$ group, wherein $X_6$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

7. The method of claim 4, wherein the at least one acidic polymer has the structure of Structure V:

(V);

wherein each monomer $B_1$ through $B_M$ is a monomer having a structure independently selected from Structures VI, VII, or VIII, M is the average number of monomer units of the at least one acidic polymer, Structures VI, VII, and VIII, respectively, have the following structures:

(VI)

(VII)

(VIII)

wherein each $Z_4$, $Z_5$, and $Z_6$ is independently a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl group, a carbonate group, an acetal group, a ketal group, a siloxyl group, a carboxylic acid group, a carboxylic acid anhydride group, a carboxylic acid anhydride half-ester group, an ether group, an amide group, a carbamate group, a thioether group, a fluorinated linear alkylene, a fluorinated branched alkylene, a fluorinated cyclic alkylene, a polycyclic alkylene, a fluorinated linear heteroalkylene, a fluorinated branched heteroalkylene, a fluorinated cyclic heteroalkylene, a fluorinated polycyclic heteroalkylene, a fluorinated ester group, a fluorinated carbonyl group, a fluorinated carbonate group, a fluorinated acetal group, a fluorinated ketal group, a fluorinated siloxyl group, a fluorinated carboxylic acid group, a fluorinated carboxylic acid anhydride group, a fluorinated carboxylic acid anhydride half-ester group, a fluorinated ether group, a fluorinated amide group, a fluorinated carbamate group, or a fluorinated thioether group;

wherein $R_4$ is a sulfonic acid group, a sulfinic acid group, a carboxylic acid group, a $C_5$ to $C_{10}$ aromatic or heteroaromatic group, or a $—X_4—Y_4$ group, wherein $X_4$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl groups, an amide group, an ether group, a thioether group, a carbonate group, a carbamate group, an acetal group, or a ketal group and $Y_4$ is a sulfonic acid group, a sulfinic acid group, or a carboxylic acid group;

wherein $R_5$ is hydrogen, fluorine, a fluoroalcohol group, a sulfonamide group, a phenolic group, a naphtholic group, a carboxylic acid group, a sulfonic acid group, a lactone group, a $C_5$ to $C_{10}$ aromatic or heteroaromatic group, or a $—X_5—Y_5$ group, wherein $X_5$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_5$ is a fluoroalcohol group, a sulfonamide group, a phenolic group, a naphtholic group, a carboxylic acid group, or a sulfonic acid group; and wherein $R_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycylic heteroalkane, a $C_5$ to $C_{10}$ aromatic or heteroaromatic group, or an —$X_6$—$Y_6$ group, wherein $X_6$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

8. The method of claim 1, wherein the substrate is a woven fabric, a nonwoven fabric, a foam, or one or more of any combination thereof.

9. The method of claim 1, wherein the substrate is a gauze, a net, a mesh, a fleece, a foam, or one or more of any combination thereof.

10. The method of claim 1, wherein the substrate is formed of cotton, a cellulose derived polymer, a polyolefin, a polyester, a polyamide, a polyester, a polyurethane, a polybutadiene, an elastomer of polybutadiene or polyurethane, a polyacrylamide, a polyacrylonitrile, an acrylic, an acrylate, Karaya gum, or a polysaccaride.

11. The method of claim 1, wherein the substrate is a woven or nonwoven fabric comprising fibers formed of cellulose acetate, a polyester, nylon, rayon, a rayon/polyester blend, a polyester/cotton blend, cotton, or any combination thereof.

12. The method of claim 1, wherein the substrate comprises a gauze formed of cotton, cellulose acetate, or a combination thereof.

13. The method of claim 1, wherein the substrate comprises a hydrophilic material.

14. A method of making a wound dressing comprising:
applying a mixture of at least one class A polymer and at least one class B polymer onto a surface of an absorbent substrate, and
curing the polymer mixture disposed on the absorbent substrate to form a low-adherence layer,
the at least one class A polymer having a fluorine content greater than the fluorine content of the at least one class B polymer, and the at least one class A polymer having the structure of Structure IX and the at least one class B polymer having the structure of Structure X as follows:

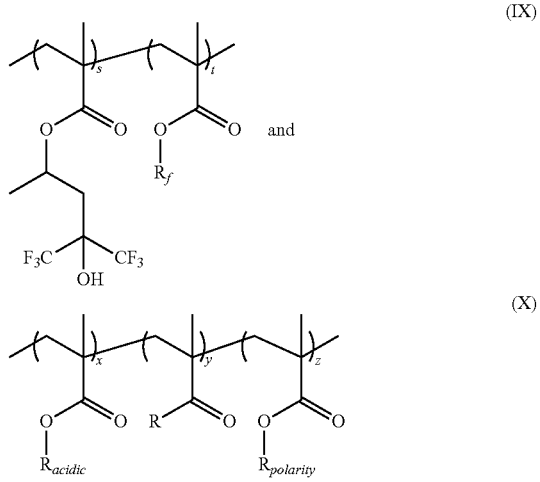

wherein $R_f$ is selected from $R_1$, $R_2$, or $R_3$; $R_{acidic}$ is selected from $R_4$ or $R_5$; $R_{polarity}$ is different from $R_{acidic}$ and selected from $R_5$ or $R_6$; R is different from $R_{acidic}$ and $R_{polarity}$ and is selected from $R_5$; s is any number from 0 to 100 and t is any number from 0 to 100, such that s+t is greater than or equal to 50 and less than or equal to 100; and x is any number from 0 to 99.9, y is any number from 0.1 to 99.9, and z is any number from 0 to 99.9, such that x+y+z is greater than or equal to 50 and less than or equal to 100;

wherein $R_1$ is a fluoroalcohol group, a fluoroalcohol group protected with an acid-labile group, a fluoroalcohol group protected with a base-labile group, a fluoroalcohol group protected with an acid-labile fluorinated group, a fluoroalcohol group protected with a base-labile fluorinated group, a lactone group, a $C_5$ to $C_{10}$ aromatic or heteroaromatic group, or an —$X_1$—$Y_1$ group, wherein $X_1$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_1$ is a fluoroalcohol group, a fluoroalcohol group protected with an acid-labile group a fluoroalcohol group protected with a base-labile group, a fluoroalcohol group protected with an acid-labile fluorinated group, or a fluoroalcohol group protected with a base-labile fluorinated group;

wherein $R_2$ is hydrogen, fluorine, a fluoroalcohol group, a sulfonamide group, a phenolic group, a naphtholic group, a carboxylic acid group, a sulfonic acid group, a $C_5$ to $C_{10}$ aromatic or heteroaromatic group, or an —$X_2$—$Y_2$ group, wherein $X_2$ is a linear alkylene, a branched alkylene, a cyclic alkylene, a polycyclic alkylene, a linear heteroalkylene, a branched heteroalkylene, a cyclic heteroalkylene, polycylic heteroalkylene, an ester group, a carbonyl group, an amide group, an ether group, a thioether group, a carbonate group, a carbamate group, an acetal group, or a ketal group and $Y_2$ is a fluoroalcohol group, a sulfonamide group, a phenolic group, a naphtholic group, a carboxylic acid group, or a sulfonic acid group;

wherein $R_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycyclic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycyclic heteroalkane, a $C_5$ to $C_{10}$ aromatic or heteroaromatic group, or a —$X_3$—$Y_3$ group, wherein $X_3$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_3$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycylic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane;

wherein $R_4$ is a sulfonic acid group, a sulfinic acid group, a carboxylic acid group, a $C_5$ to $C_{10}$ aromatic or hetero aromatic group, or a —$X_4$—$Y_4$ group, wherein $X_4$ is a linear alkylene, a branched alkylene, a cyclic alkylene, a polycyclic alkylene, a linear heteroalkylene, a branched heteroalkylene, a cyclic heteroalkylene, a polycyclic heteroalkylene, an ester group, a carbonyl groups, an amide group, an ether group, a thioether group, a carbonate group, a carbamate group, an acetal group, or a ketal group and $Y_4$ is a sulfonic acid group, a sulfinic acid group, or a carboxylic acid group;

wherein $R_5$ is hydrogen, fluorine, a fluoroalcohol group, a sulfonamide group, a phenolic group, a naphtholic group, a carboxylic acid group, a sulfonic acid group, a lactone group, a $C_5$ to $C_{10}$ aromatic or hetero aromatic group, or a —$X_5$—$Y_5$ group, wherein $X_5$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_5$ is a fluoroalcohol group, a sulfonamide group, a phenolic group, a naphtholic group, a carboxylic acid group, or a sulfonic acid group; and wherein $R_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycyclic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, a fluorinated polycylic heteroalkane, a $C_5$ to $C_{10}$ aromatic or heteroaromatic group, or an —$X_6$—$Y_6$ group, wherein $X_6$ is a linear alkylene, a branched alkylene, a cyclic alkylene, a polycyclic alkylene, a linear heteroalkylene, a branched heteroalkylene, a cyclic heteroalkylene, a polycylic heteroalkylene, an ester group, a carbonyl group, an amide group, an ether group, a thioether group, a carbonate group, a carbamate group, an acetal group, or a ketal group and $Y_6$ is hydrogen, fluorine, an acid-labile group, a base-labile group, an acid-labile fluorinated group, a base-labile fluorinated group, a linear alkane, a branched alkane, a cyclic alkane, a polycyclic alkane, a linear heteroalkane, a branched heteroalkane, a cyclic heteroalkane, a polycyclic heteroalkane, a fluorinated linear alkane, a fluorinated branched alkane, a fluorinated cyclic alkane, a fluorinated polycyclic alkane, a fluorinated linear heteroalkane, a fluorinated branched heteroalkane, a fluorinated cyclic heteroalkane, or a fluorinated polycylic heteroalkane.

15. The method of claim 14, wherein R is selected from:

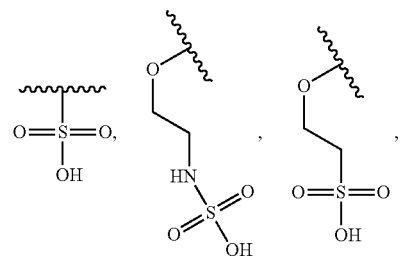

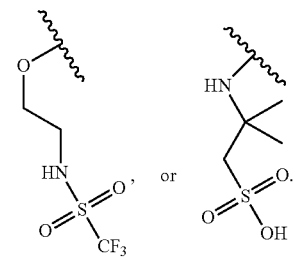

16. The method of claim 14, wherein R is selected from:

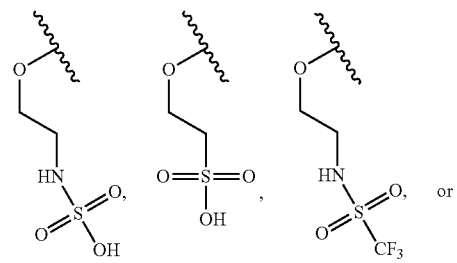

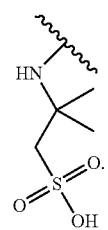

17. The method of claim 14, wherein R is selected from:

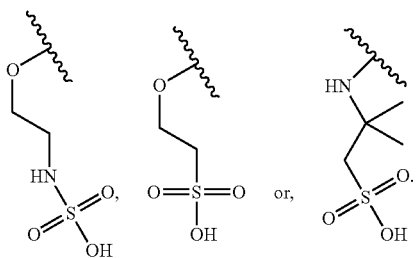

18. The method of claim 14, wherein R is selected from:

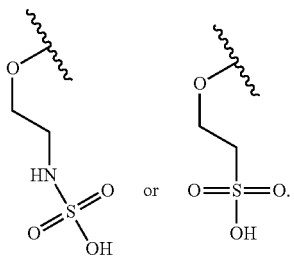 [SMILES: *OCCNS(=O)(=O)O ; *OCCS(=O)(=O)O]

19. The method of claim 14, wherein $R_f$ is selected from: —H, —CH$_3$,

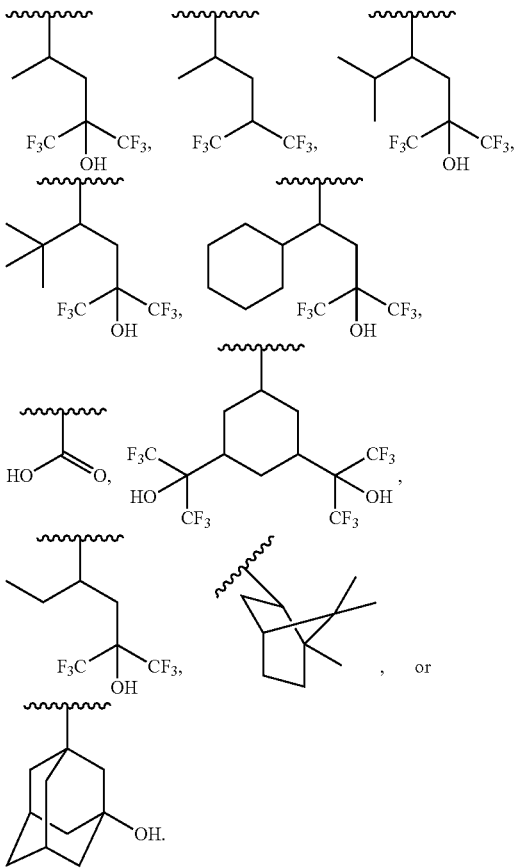

20. The method of claim 14, wherein $R_{acidic}$ is selected from:

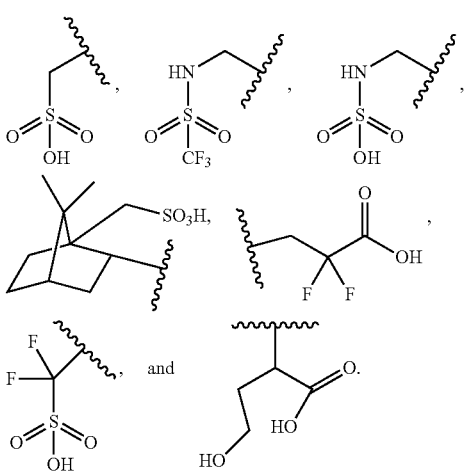

21. The method of claim 14, wherein $R_{polarity}$ is selected from:

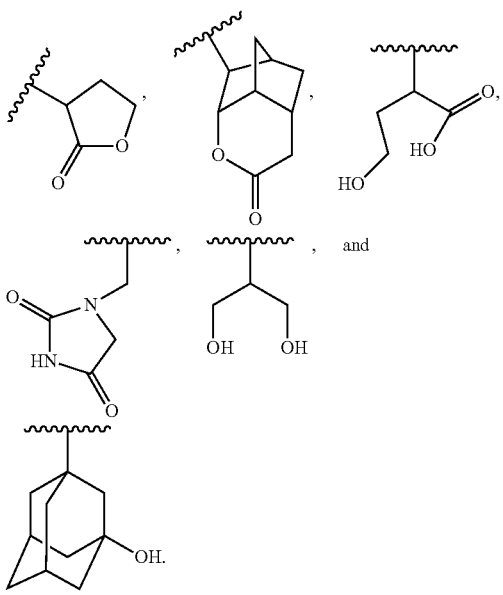

22. The method of claim 14, wherein the substrate is a woven fabric, a nonwoven fabric, a foam, or one or more of any combination thereof.

23. The method of claim 14, wherein the substrate is a gauze, a net, a mesh, a fleece, a foam, or one or more of any combination thereof.

24. The method of claim 14, wherein the substrate is formed of cotton, a cellulose derived polymer, a polyolefin, a polyester, a polyamide, a polyester, a polyurethane, a polybutadiene, an elastomer of polybutadiene or polyurethane, a polyacrylamide, a polyacrylonitrile, an acrylic, an acrylate, Karaya gum, or a polysaccharide.

25. The method of claim 14, wherein the substrate is a woven or nonwoven fabric comprising fibers formed of cellulose acetate, a polyester, nylon, rayon, a rayon/polyester blend, a polyester/cotton blend, cotton, or any combination thereof.

26. The method of claim 14, wherein the substrate comprises a cotton gauze.

27. The method of claim 14, wherein the substrate comprises a hydrophilic material.

28. The method of claim 1, further comprising applying an outer layer onto another surface of the substrate, the outer layer being a conformable film, a conformable elastically extensible net, or a conformable backing material.

29. The method of claim 14, further comprising applying an outer layer onto another surface of the substrate, the outer layer being a conformable film, a conformable elastically extensible net, or a conformable backing material.

\* \* \* \* \*